(12) United States Patent
Wagealla et al.

(10) Patent No.: US 9,700,512 B1
(45) Date of Patent: Jul. 11, 2017

(54) SYNTHESIS OF HESPERETIN NANOPARTICLES

(71) Applicant: KING SAUD UNIVERSITY, Riyadh (SA)

(72) Inventors: Mai Abdelrahman Elobeid Wagealla, Riyadh (SA); Lulwah Saleh Mohammed Al-Hassan, Riyadh (SA); Manal Ahmed Gasmelseed Awad, Riyadh (SA); Nouf Abdullah Mureet Al-Ghamdi, Riyadh (SA); Promy Virk, Riyadh (SA); Awatif Ahmed Hendi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/151,454

(22) Filed: May 10, 2016

(51) Int. Cl.
*A61K 31/353* (2006.01)
*A61K 9/14* (2006.01)
(52) U.S. Cl.
CPC .............. *A61K 9/14* (2013.01); *A61K 31/353* (2013.01)

(58) Field of Classification Search
CPC ..................................................... A61K 31/353
USPC ......................................................... 514/456
See application file for complete search history.

(56) References Cited

U.S. PATENT DOCUMENTS 8,642,087 B1    2/2014  Dziubla et al.

OTHER PUBLICATIONS

Kakran et al., "Fabrication of Nanoparticles of Silymarin, Hesperetin and Glibenclamide by Evaporative Precipitation of Nanosuspension for Fast Dissolution," Pharm Anal Acta, 2015, vol. 6, pp. 1-7.

*Primary Examiner* — Jennifer M Kim
(74) *Attorney, Agent, or Firm* — Richard C. Litman

(57) ABSTRACT

A method of preparing hesperetin nanoparticles includes dissolving hesperetin in an organic solvent to form a solution; spraying the solution in boiling water while applying ultrasonic energy to form a mixture; and stirring the mixture for at least about 15 minutes at a speed of about 200-800 rpm to obtain the hesperetin nanoparticles.

5 Claims, 13 Drawing Sheets

SYNTHESIS OF HESPERETIN NANOPARTICLES

BACKGROUND OF THE INVENTION

1. Field of the Invention

The present invention relates to bio-nanotechnology and, particularly, to a method of synthesizing hesperetin non-metal nanoparticles for use in antioxidant therapy to treat lead-induced stress in mammals.

2. Description of the Related Art

Lead is a major human health hazard and a confirmed multi-target toxicant with effects on the gastrointestinal, haematopoietic, cardiovascular, nervous, immune, reproductive and excretory systems. Lead indirectly contributes to oxidative stress. Biological compounds with antioxidant properties contribute to protection of cells and tissues against deleterious effects of reactive oxygen species (ROS). Moreover, lead inhibits the activities of the antioxidant defense system, including superoxide dismutase (SOD), catalase (CAT), and glutathione peroxidase (GSH-Px), as well as reduction of glutathione (GSH), which will increase the susceptibility of cells to free radical-induced toxicity. Metallothioneins (MT) are cysteine-rich, metal-binding proteins that are readily induced by various physiologic and toxicologic stimuli. It is generally accepted that MT is an important defense against the detoxification of non-essential metals. Susceptibility to lead toxicity increases in animals that are unable to synthesize metallothionein. Furthermore, it is suggested that one of the basic mechanisms involved in metal-induced toxicity is via the increased level of lipid peroxidation (LP) resulting in variation of homeostasis including but not limited to the lipid profile.

Nanoparticles are particularly useful in drug delivery for water-insoluble compounds, e.g., cyclosporine A and coenzyme Q10, because the size of nanoparticles (less than 100 nm) can increase absorption and bioavailability of the delivered drug.

Thus, a method of producing eco-friendly non-metal nanoparticles for treating lead induced oxidative stress in an organism solving the aforementioned problems is desired.

SUMMARY OF THE INVENTION

A method of preparing hesperetin includes dissolving hesperetin, e.g., bulk hesperetin, in an organic solvent to form a solution; adding the solution to boiling water under ultrasonic conditions to form a mixture; and stirring the mixture for about 20 to about 30 minutes. The organic solvent can be at least one of methanol, ethanol, dichloromethane, and chloroform.

A method of treating lead-induced oxidative stress in a mammal can include administering an effective amount of hesperetin nanoparticles to the mammal.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

A method of preparing hesperetin nanoparticles includes dissolving hesperetin in an organic solvent to form a solution; adding the solution to boiling water under ultrasonic conditions to form a mixture; and stirring the mixture for at least about 15 minutes, e.g., about 20 to about 30 minutes, at a speed of about 200-800 rpm to obtain the hesperetin nanoparticles. The mixture can be sonicated for about 10 minutes to about 20 minutes prior to stirring. The hesperetin nanoparticles can be isolated in any suitable manner known in the art, e.g., centrifugation and/or filtration. Ultrasonic conditions can include applying ultrasonic energy at a frequency of 30-60 kHz with a power of about 100 watts. The organic solvent can include at least one of methanol, ethanol, dichloromethane and chloroform. The nanoparticle solution (about 1 ml to about 2 ml) can be sprayed dropwise into the boiling water (about 50 to about 70 ml) at a rate of about 0.2 ml/minute to about 0.4 ml/minute in about five minutes. The mixture can be stirred at room temperature, e.g., about 24° C.

Hesperetin nanoparticles prepared by the present method can possess a mean diameter in the range of from about 50 nm to about 200 nm. The hesperetin nanoparticles can have spherical, spheroidal, elongated spherical, rod-shaped, and/or faceted shapes. The hesperetin nanoparticles can be used for treating oxidative stress in mammals, e.g., oxidative stress caused by the presence of lead. An effective amount of hesperetin nanoparticles can be administered to an organism suffering from oxidative stress caused by the presence of lead. The organism can be a human or animal.

As used herein, the term "nanoparticle" refers to a particle having at least one dimension and sized between 1 and 100 nanometers. The nanoparticles can include hesperetin nanoparticles. In some embodiments, the nanoparticles disclosed herein are from about 5 nm to about 500 nm in diameter, e.g., about 100 nm to about 200 nm. As used herein, ultrasonication refers to irradiation with ultrasonic (>20 kHz) waves. Ultrasonication may be performed using an ultrasonic bath or an ultrasonic probe.

Hesperetin (5,7,3'-trihydroxy-4-methoxyl flavanone), is one of the most abundant flavonoid antioxidants found in citrus fruits. It shows a wide spectrum of pharmacological effects, including, anti-inflammatory, and antioxidant properties. Its chemical structure is depicted below:

Hesperetin is a well-documented antioxidant compound and its bioactivity has been attributed to its structure-activity relationship. In spite of its proven pharmacological actions in humans, bulk hesperetin has failed to become a main line drug because of its low oral bioavailability from conventional dosage forms. Hesperetin has been known to inhibit the maturation and function of monocyte-derived dendritic cells from patients with asthma, protection against cardiovascular disease, and affect hepatic fatty acid oxidation in rats by acting as pro-oxidant agents. Also, the protective effect of hesperetin in rat models of partial sciatic nerve ligation has been shown. Hesperetin is known to inhibit rat coronary constriction by inhibiting $Ca^{2+}$ influx and enhancing voltage-gated $K^+$ channel currents of the myocytes, rescues retinal oxidative stress, neuroinflammation and apoptosis in diabetic rats, protects against cardiac remodeling induced by pressure overload in mice.

The hesperetin nanoparticles are non-metal nanoparticles that can be useful for treating oxidative stress, e.g., oxidative stress caused by lead exposure or lead toxicity, in an organism. The organism can be an animal. The organism can be a human or other mammal.

The present technology, thus generally described, will be understood more readily by reference to the following examples, which is provided by way of illustration and is not intended to limit the scope of the present technology.

EXAMPLE 1

Synthesis of Hesperetin Nanoparticles in Chloroform

Figure 1A:
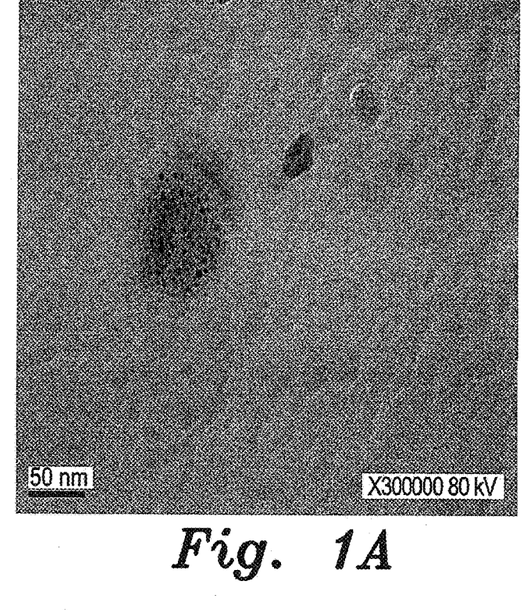
FIGS. 1A-1B show the transmission electron micrograph (TEM) images of the chloroform-hesperetin nanoparticles.
Figure 1B:
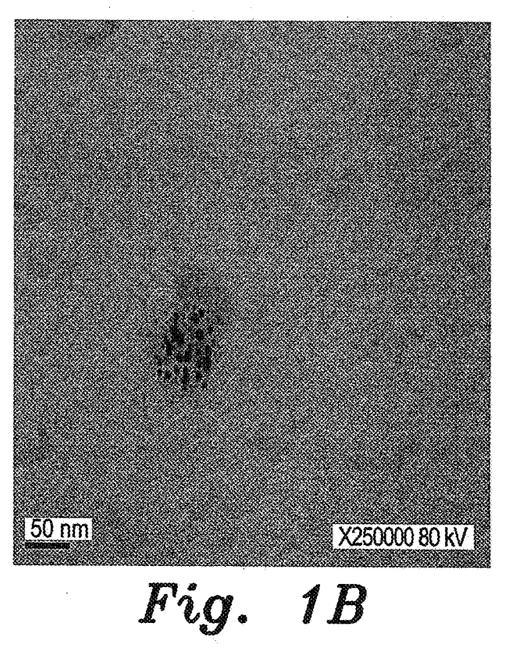
Figure 2:
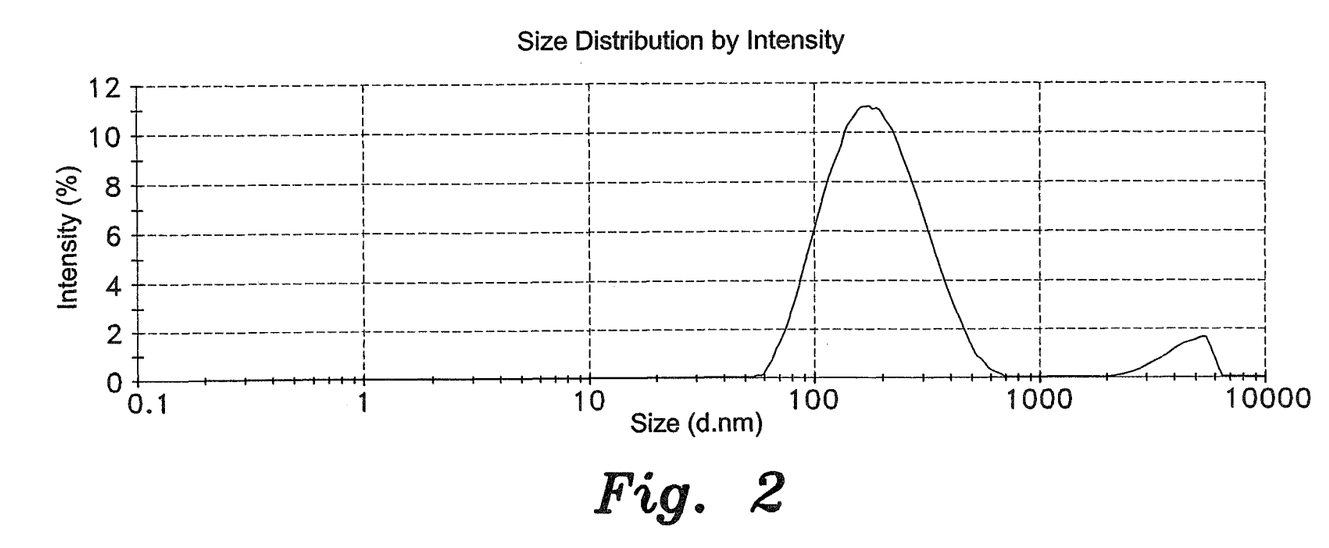
FIG. 2 shows the particle size distribution by intensity (Zetasizer) of the chloroform-hesperetin nanoparticles.

About 50-100 mg of hesperetin powder was dissolved in about 20-25 ml chloroform. About 1-2 ml of the hesperetin-chloroform solution was sprayed into about 50-70 mL boiling water, dropwise, with a flow rate of 0.2-0.4 mL/min in 5 min under ultrasonic conditions. After sonication for about 10-20 minutes, the solution was then stirred at about 200-800 rpm at room temperature for about 20-30 minutes to obtain hesperetin nanoparticles. FIGS. 1A-1B show the transmission electron micrograph (TEM) images of the chloroform-hesperetin nanoparticles. The chloroform-hesperetin nanoparticles are spherical or rod shaped as shown in FIGS. 1A-1B. FIG. 2 shows the hesperetin particle size distribution by intensity of the chloroform-hesperetin nanoparticles, indicating the average particle size to be about 200 nm.

EXAMPLE 2

Synthesis of Hesperetin Nanoparticles in Dichloromethane

Figure 3A:
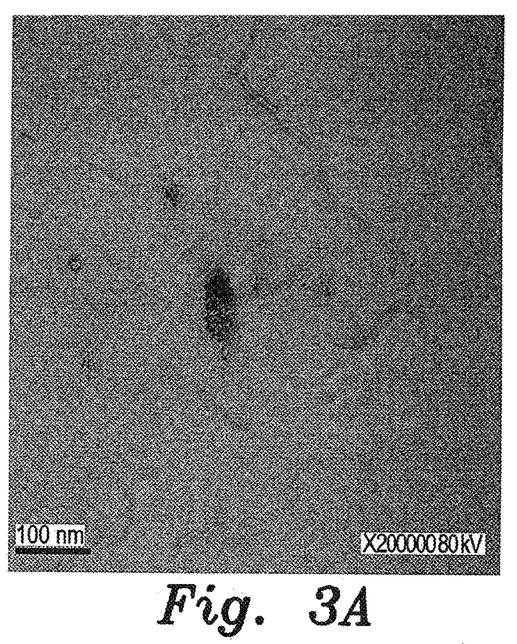
FIGS. 3A-3B-show the TEM images of the dichloromethane-hesperetin nanoparticles.
Figure 3B:
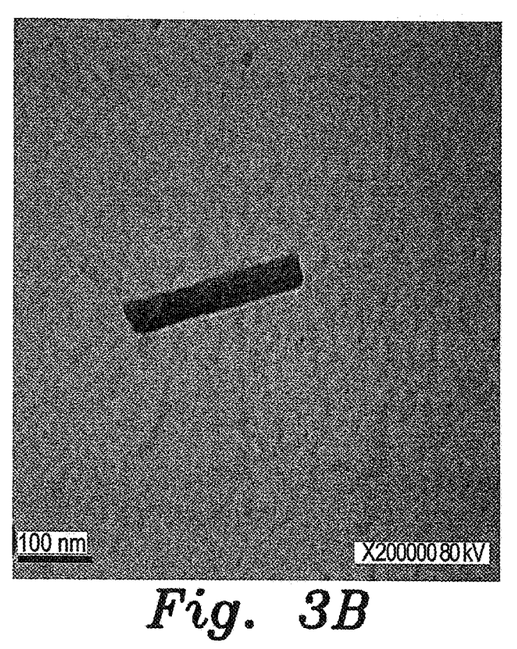
Figure 4:
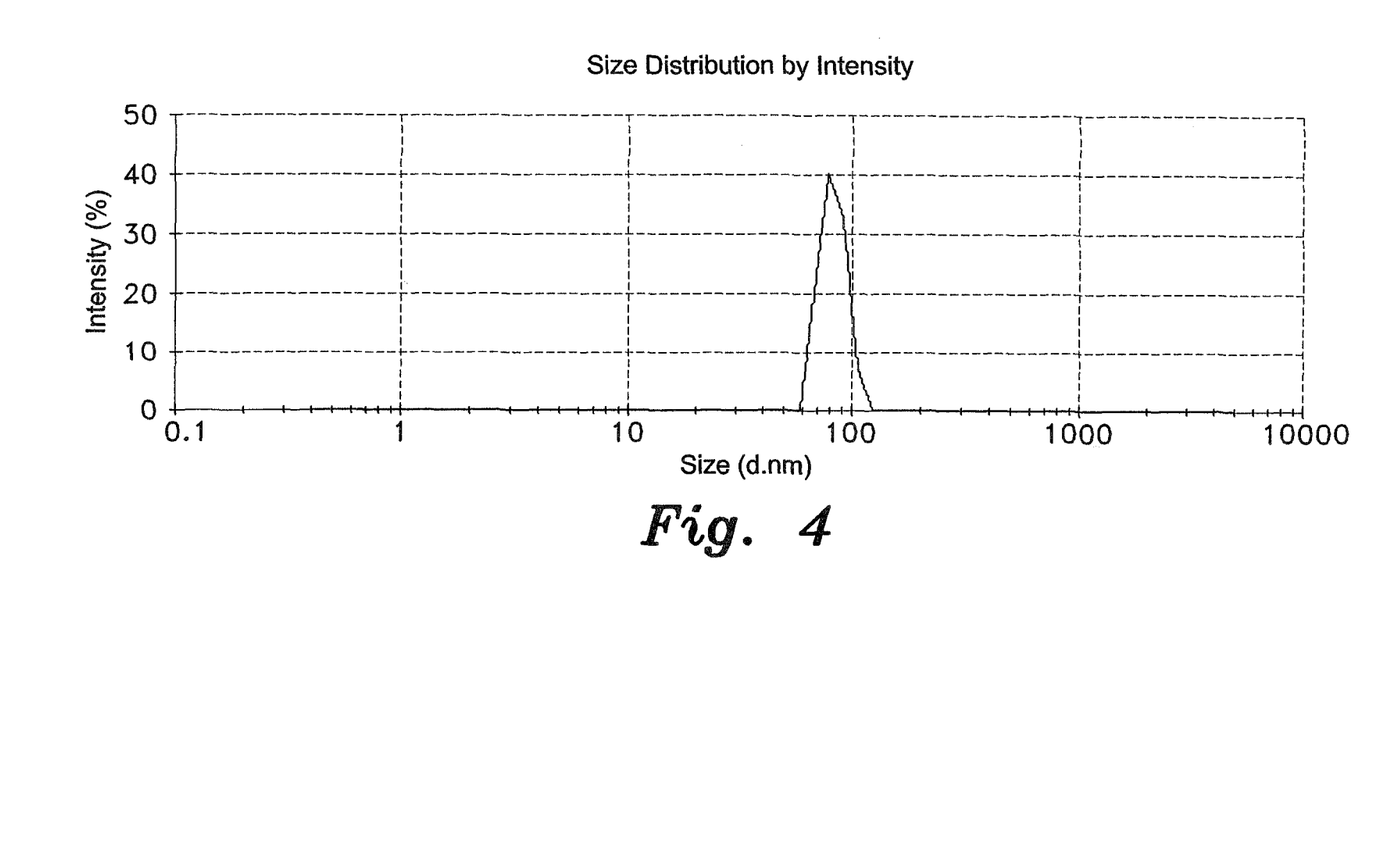
FIG. 4 shows the shows the particle size distribution by intensity (Zetasizer) of the dichloromethane-hesperetin nanoparticles.

About 50-100 mg of hesperetin powder was dissolved in about 20-25 ml dichloromethane. About 1-2 ml of the hesperetin-dichloromethane solution was sprayed into about 50-70 mL boiling water, dropwise, with a flow rate of 0.2-0.4 mL/min in 5 min under ultrasonic conditions. After sonication for about 10-20 minutes, the solution was then stirred at about 200-800 rpm at room temperature for about 20-30 minutes to obtain dichloromethane-hesperetin nanoparticles. FIGS. 3A-3B show the transmission electron micrograph (TEM) images of the dichloromethane-hesperetin nanoparticles. The dichloromethane-hesperetin nanoparticles are elongated or rod shaped as shown in FIGS. 3A-3B. FIG. 4 shows the hesperetin particle size distribution by intensity of the dichloromethane hesperetin nanoparticles, indicating the average particle size to be about 80 nm.

EXAMPLE 3

Synthesis of Hesperetin Nanoparticles in Ethanol

Figure 5A:
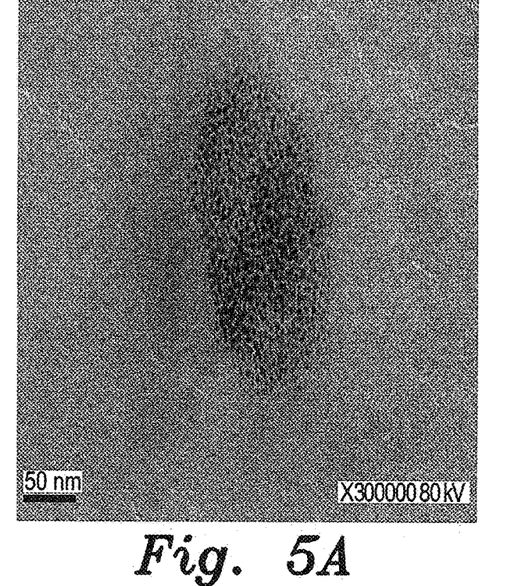
FIGS. 5A-5B shows the TEM images of the ethanol-hesperetin nanoparticles.
Figure 5B:
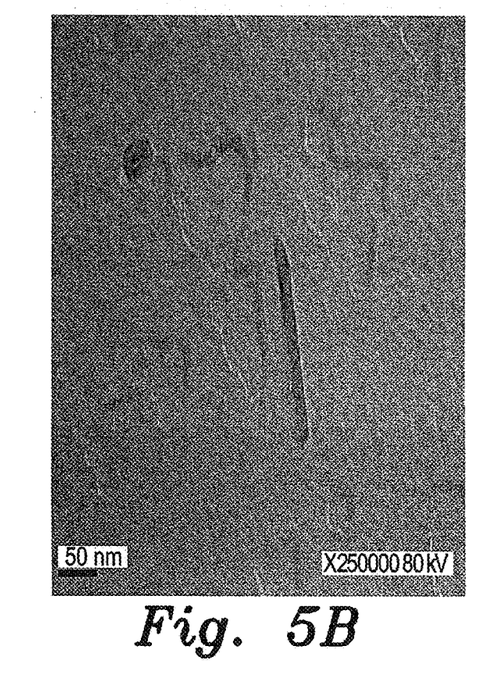
Figure 6:
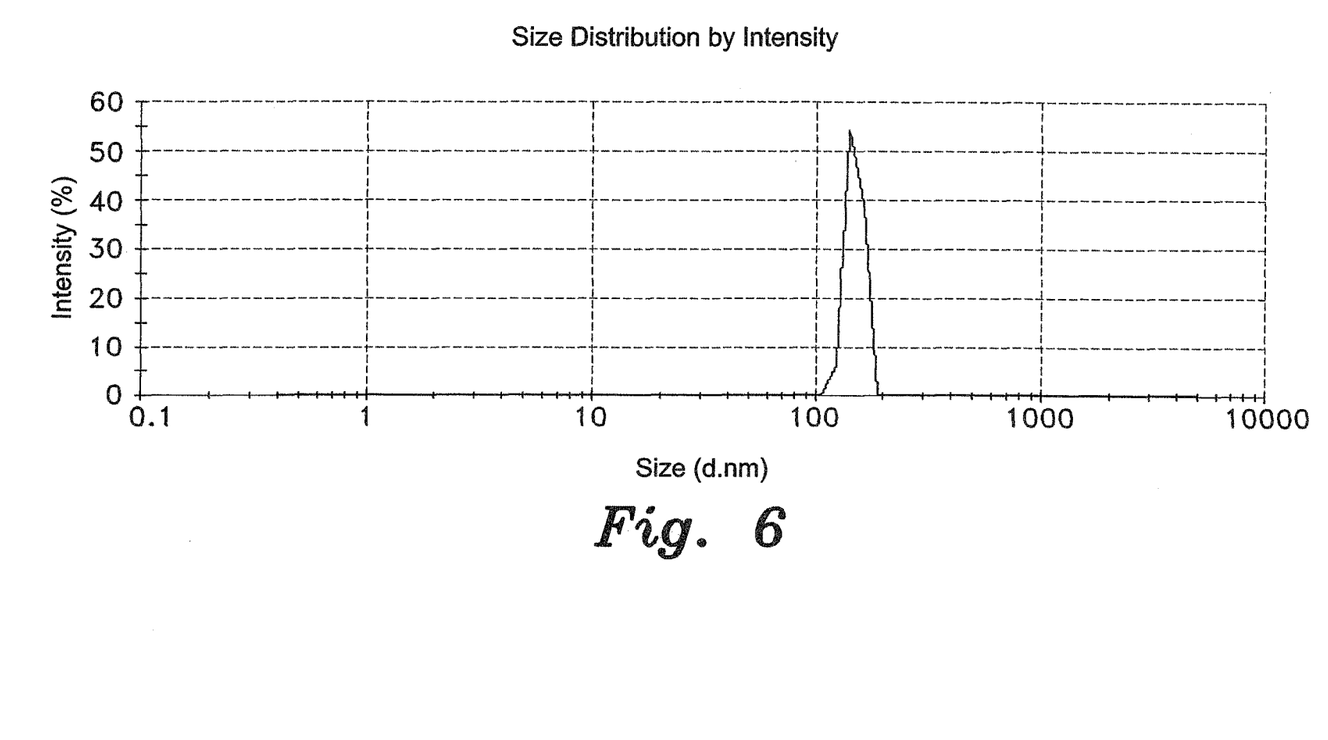
FIG. 6 shows the particle size distribution by intensity (Zetasizer) of the ethanol-hesperetin nanoparticles.

About 50-100 mg of hesperetin powder was dissolved in about 20-25 ml ethanol. About 1-2 ml of the hesperetin-ethanol solution was sprayed into about 50-70 mL boiling water, dropwise, with a flow rate of 0.2-0.4 mL/min in 5 min under ultrasonic conditions. After sonication for about 10-20 minutes, the solution was then stirred at about 200-800 rpm at room temperature for about 20-30 minutes to obtain ethanol-hesperetin nanoparticles. FIGS. 5A-5B show the TEM images of the ethanol-hesperetin nanoparticles that can be spherically clustered or rod shaped. FIG. 6 shows the ethanol-hesperetin particle size distribution by intensity of the ethanol-hesperetin nanoparticles, indicating the average particle size to be about 150 nm.

EXAMPLE 4

Synthesis of Hesperetin Nanoparticles in Methanol

Figure 7A:
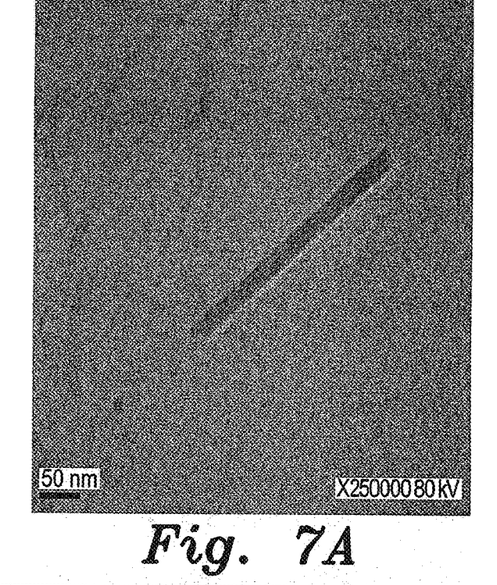
FIG. 7A-7B show the TEM images of the chloroform-hesperetin nanoparticles.
Figure 7B:
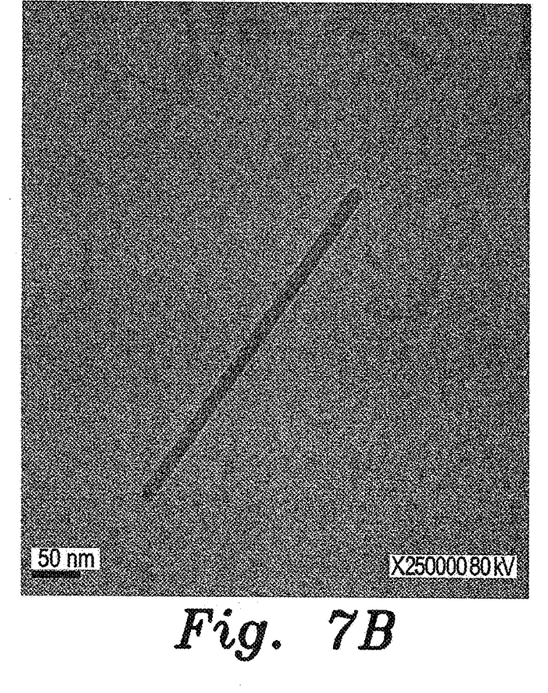
Figure 8:
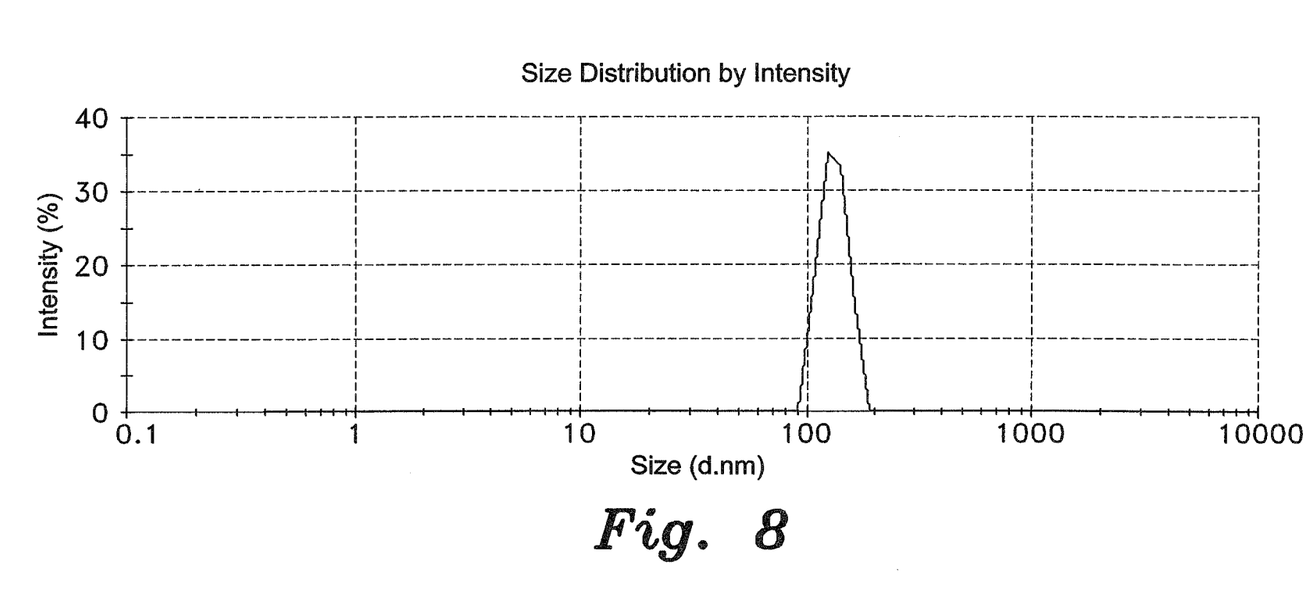
FIG. 8 shows the particle size distribution by intensity (Zetasizer) of the chloroform-hesperetin nanoparticles.

About 50-100 mg of hesperetin powder was dissolved in about 20-25 ml methanol. About 1-2 ml of the hesperetin-methanol solution was sprayed into about 50-70 mL boiling water dropwise with a flow rate of 0.2-0.4 mL/min within 5 min under ultrasonic conditions. After sonication for about 10-20 minutes, the solution was then stirred at about 200-800 rpm at room temperature for about 20-30 minutes to obtain methanol-hesperetin nanoparticles. FIGS. 7A-7B show the transmission electron micrograph (TEM) images of the methanol-hesperetin nanoparticles showing rod-like shapes. FIG. 8 shows the particle size distribution by intensity of the methanol-hesperetin nanoparticles, indicating the average particle size to be about 125 nm.

EXAMPLE 5

Experimental Design and Animal Testing

Adult Wistar rats (8-weeks old, weighing approximately 150-180 g) were randomly divided into four groups, six rats in each: 1) Group 1 untreated control was orally exposed to physiological saline. 2) Group 2 were orally exposed to lead acetate (500 mg Pb/L). 3) Group 3 were exposed to lead acetate (500 mg Pb/L) and treated orally with bulk hesperetin (50 mg/kg/day). 4) Group 4 were exposed to lead acetate (500 mg Pb/L) and treated orally with nano particles of hesperetin (50 mg/kg/day). The experimental period was for twelve weeks, after which, blood samples were collected from all animals to assess the blood profiles and metal accumulation in various tissues in the Wistar rats.

Figure 9:
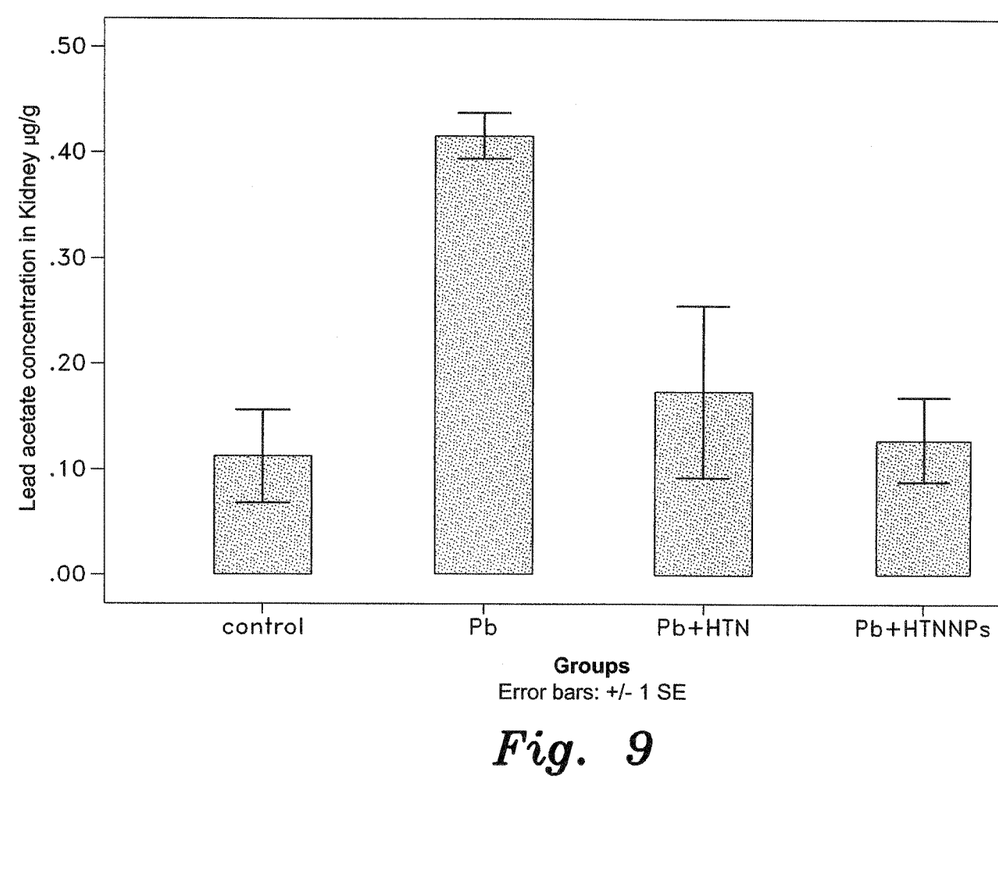
FIG. 9 shows the lead concentration in kidney of experimental rats.
Figure 10:
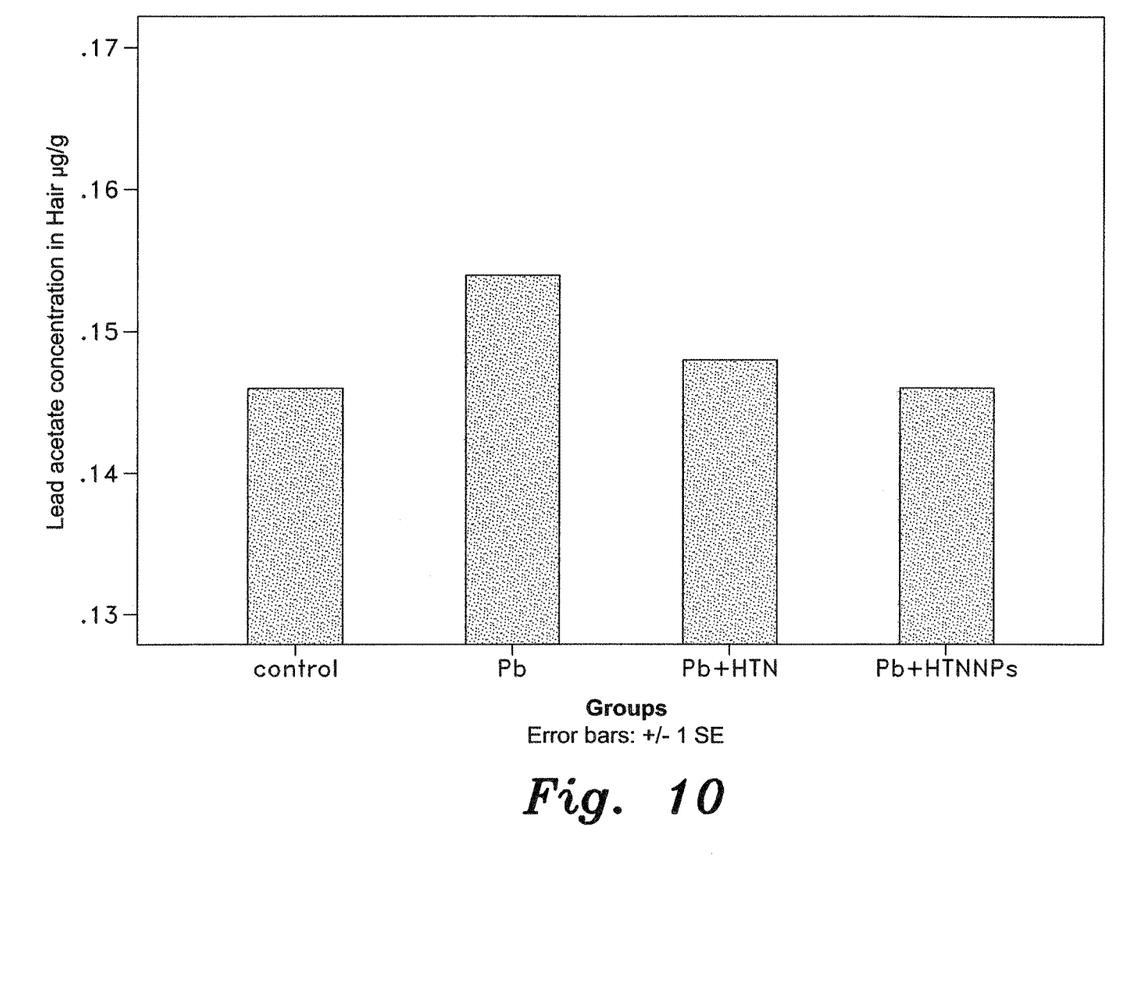
FIG. 10 shows the lead concentration ($\mu$g/g) in hair of experimental rats.

FIG. 9 shows the lead concentration in the kidney of experimental rats. FIG. 10 shows the lead concentration (μg/g) in the hair of the experimental rats. After the experimental lead exposure, it was found that there was an increase in lead concentration in the group exposed to Pb only. Treatment with hesperetin nanoparticles reduced the lead concentration in the kidney and hair tissues when compared to the group exposed to Pb only as illustrated in FIGS. 9 and 10.

Figure 11A:
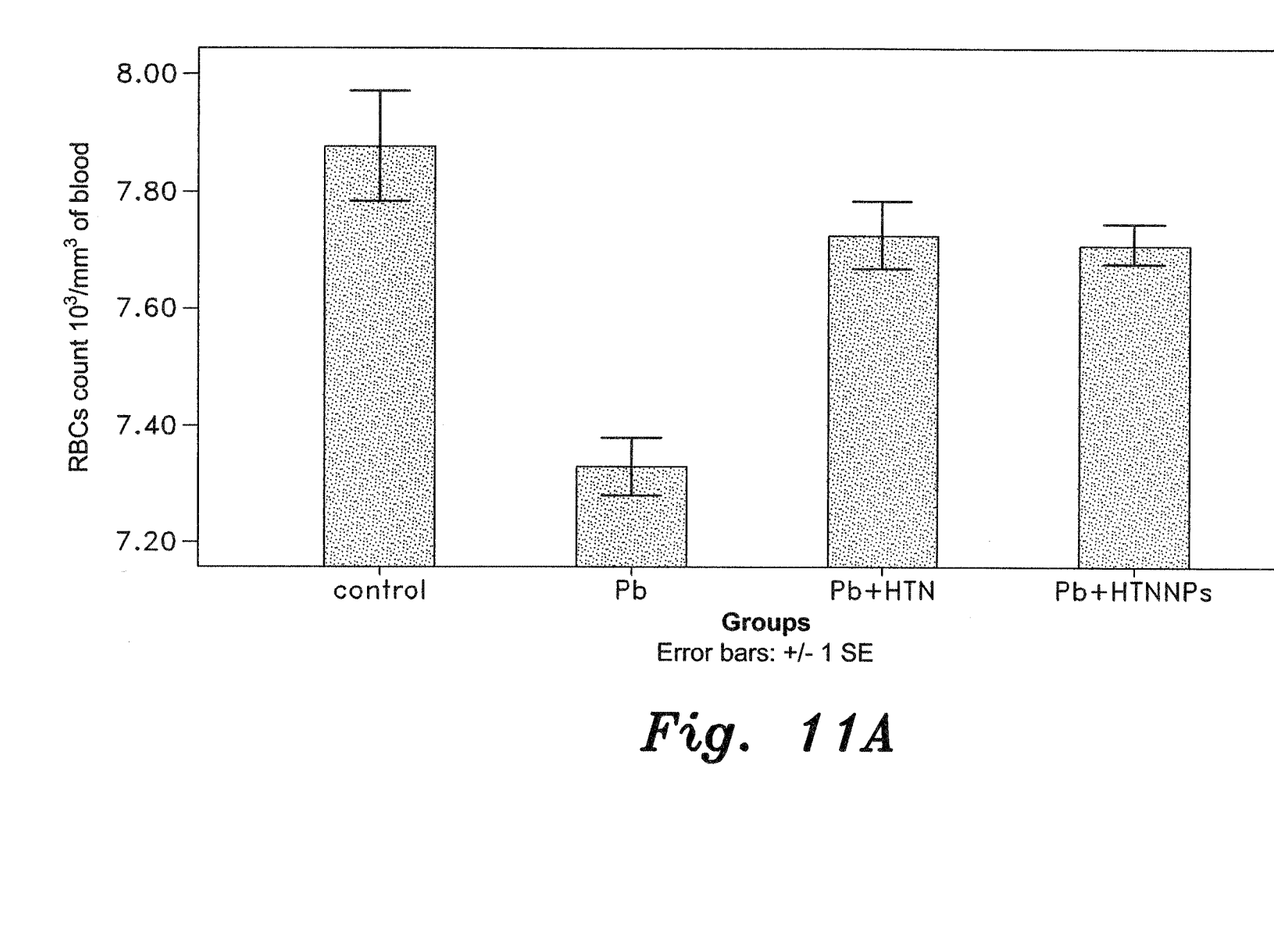
FIG. 11A-C shows the red blood cell (RBC) and white blood cell (WBC) count ($10^3/mm^3$) and HGB (g/dl) levels in blood of experimental rats respectively.
Figure 11B:
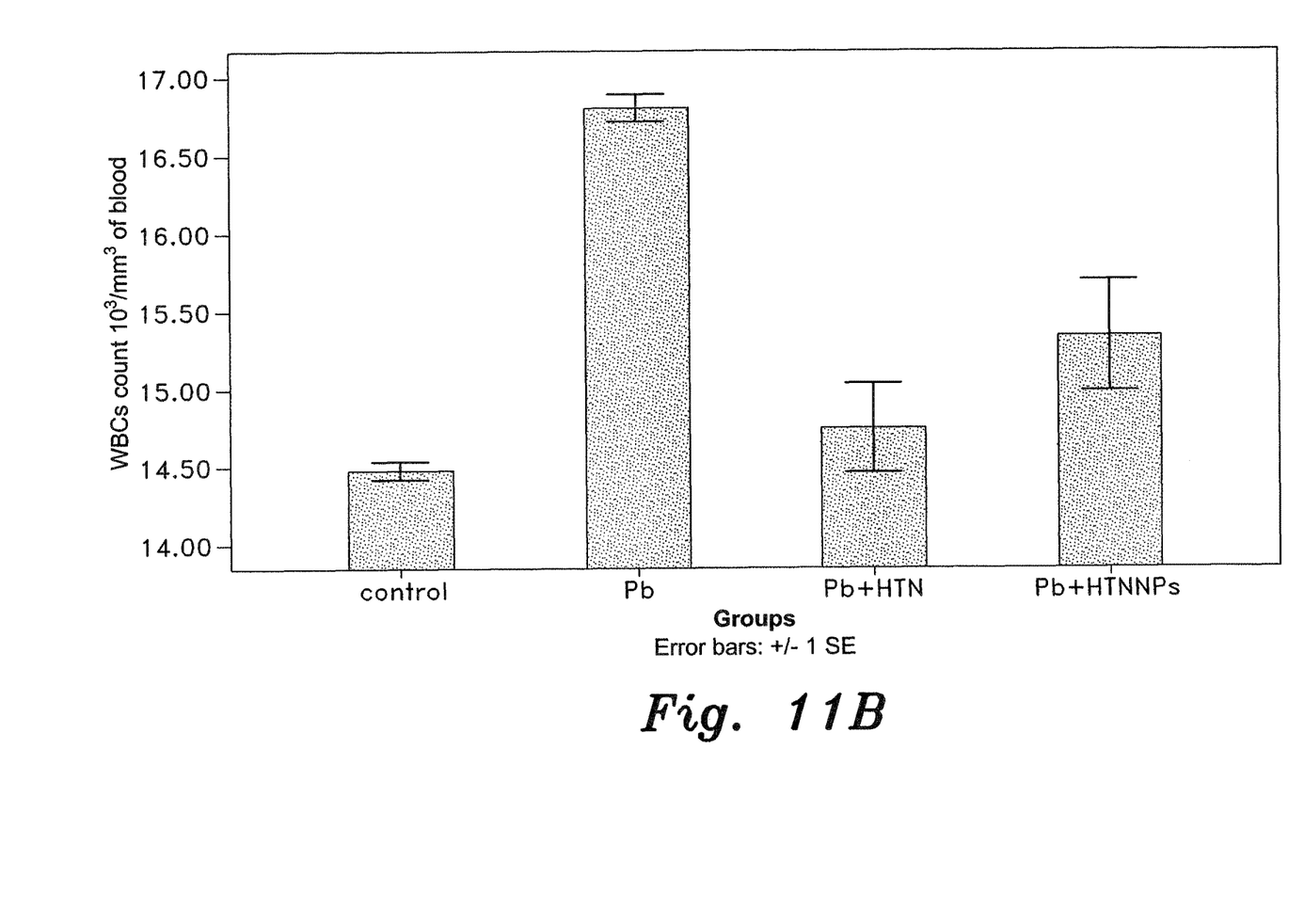
Figure 11C:
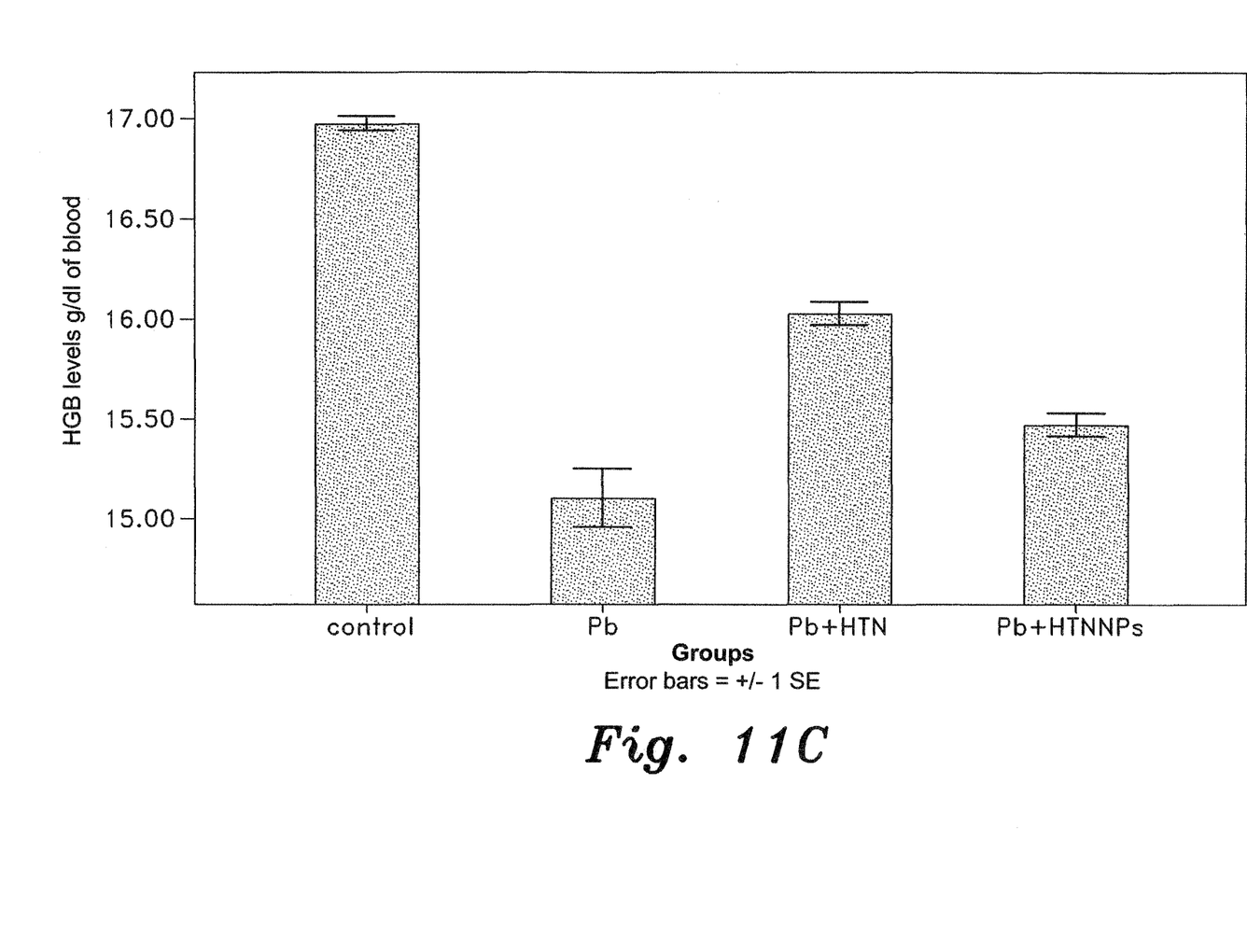

FIGS. 11A-C shows the red blood cell (RBC) and white blood cell (WBC) count ($10^3/mm^3$) and hemoglobin (HGB) (g/dl) levels in the blood of experimental rats respectively. After the experimental lead exposure, it was found that there was an increase in lead concentration in the Group exposed to Pb only. However, the mean of white blood cells count was higher in the group exposed to Pb only, in comparison to the control. Rats exposed to lead and treated with hesperetin nanoparticles showed an increase in the levels of hemoglobin (HGB) and red blood cells (RBCS) count. Further, the nano treatments showed a decrease in the white blood cells (WBCs) count in comparison to the non-treated Pb exposed group. (FIG. 11 A-C).

It is to be understood that the present invention is not limited to the embodiments described above but encompasses any and all embodiments within the scope of the following claims.

We claim:

1. A method of synthesizing hesperetin nanoparticles, comprising:
dissolving hesperetin in an organic solvent to form a solution;
adding the solution to boiling water under ultrasonic conditions to form a mixture; and
stirring the mixture at a temperature of about 24° C. and a speed of about 200 to about 800 rpm to obtain hesperetin nanoparticles wherein the solution is added by spraying the solution dropwise into the boiling water at a rate of about 0.2 ml/minute in about 5 minutes and wherein the hesperetin nanoparticles have a mean diameter in the range of from about 50 nm to about 200 nm.

2. The method of synthesizing hesperetin nanoparticles according to claim 1, wherein about 1 ml to about 2 ml of the solution is added to about 50 ml to about 70 ml of the boiling water.

3. The method of preparing hesperetin nanoparticles according to claim 1, wherein the organic solvent comprises at least one of methanol, ethanol, dichloromethane and chloroform.

4. The method of preparing hesperetin nanoparticles according to claim 1, wherein the mixture is sonicated for about 10 minutes to about 20 minutes prior to being stirred.

5. The method of synthesizing hesperetin nanoparticles according to claim 1, wherein the hesperetin nanoparticles have spherical, spheroidal, elongated spherical, rod-shaped, and/or faceted shapes.

* * * * *